(12) United States Patent
Chau

(10) Patent No.: US 10,525,277 B1
(45) Date of Patent: Jan. 7, 2020

(54) SKIN TREATMENT DEVICE

(71) Applicant: LALUER LLC, Pasadena, CA (US)

(72) Inventor: Nicole Chau, Pasadena, CA (US)

(73) Assignee: LALUER LLC, Pasadena, CA (US)

(*) Notice: Subject to any disclaimer, the term of this patent is extended or adjusted under 35 U.S.C. 154(b) by 0 days.

(21) Appl. No.: 16/588,874

(22) Filed: Sep. 30, 2019

Related U.S. Application Data

(60) Provisional application No. 62/789,537, filed on Jan. 8, 2019.

(51) Int. Cl.
*A61N 5/06* (2006.01)
*A61N 1/06* (2006.01)
*A61B 18/14* (2006.01)
*A61B 18/18* (2006.01)
*A61B 18/00* (2006.01)

(52) U.S. Cl.
CPC ............ *A61N 5/0616* (2013.01); *A61B 18/14* (2013.01); *A61B 18/18* (2013.01); *A61N 1/06* (2013.01); *A61B 2018/0047* (2013.01); *A61N 2005/0644* (2013.01); *A61N 2005/0651* (2013.01)

(58) Field of Classification Search
CPC ............ A61N 5/062; A61N 2005/0662; A61N 5/0624; A61N 2005/1087; A61N 2005/063; A61N 1/3603; A61N 1/0492; A61N 1/36014; A61N 1/40; A61N 5/022; A61N 1/025; A61K 41/0057; A61B 5/4848; A61B 5/4836; A61B 18/00
See application file for complete search history.

(56) References Cited

U.S. PATENT DOCUMENTS

D759,831 S   6/2016  Levi et al.
9,566,088 B2 2/2017  Ignon et al.
9,789,332 B2 10/2017 Liu et al.
(Continued)

FOREIGN PATENT DOCUMENTS

EP          3320951       5/2018
KR          10-1987328    6/2019
(Continued)

OTHER PUBLICATIONS

"ESPADA Blue Light Acne Treatment with Laser Targeting", FOREO, https://web.archive.org/eb/20171124201725/https://www.foreo.com/espada, dated Nov. 24, 2017, accessed on Oct. 7, 2019.
(Continued)

*Primary Examiner* — Deborah L Malamud
(74) *Attorney, Agent, or Firm* — Knobbe Martens Olson & Bear LLP

(57) ABSTRACT

Provided is a skincare device for providing skincare treatments to a user's skin. The skincare device has a body that includes a body having a skin-contacting surface, an ultrasound probe configured to generate ultrasound waves, radio frequency electrodes configured to generate radio frequency waves, electrical stimulation electrodes configured to generate electrical impulses and negative ions, light emitting diodes configured to emit light, and circuitry housed in the body and comprising at least one processor and at least one memory. These elements of the skincare device are arranged such that all of the electrodes are configured to contact the user's skin simultaneously and to improve contact with the user's skin. The skincare device has a plurality of treatment modes in which different combinations of elements are activated.

20 Claims, 4 Drawing Sheets

(56) References Cited

U.S. PATENT DOCUMENTS

| | | | |
|---|---|---|---|
| 9,814,906 | B2 | 11/2017 | McDaniel |
| D819,221 | S | 5/2018 | Lei |
| D840,546 | S | 2/2019 | Xiangmei |
| 10,376,693 | B2 | 8/2019 | Yamazaki |
| 2007/0198004 | A1 | 8/2007 | Altshuler et al. |
| 2010/0137752 | A1 | 6/2010 | Heine et al. |
| 2015/0224020 | A1 | 8/2015 | Flyash et al. |
| 2016/0121108 | A1 | 5/2016 | Kondo et al. |
| 2017/0036002 | A1 | 2/2017 | Ignon et al. |
| 2018/0036553 | A1 | 2/2018 | Shiibashi et al. |
| 2019/0134414 | A1 | 5/2019 | Prouza et al. |

FOREIGN PATENT DOCUMENTS

| | | |
|---|---|---|
| WO | WO 2007/106339 | 9/2007 |
| WO | WO 2009/104178 | 8/2009 |
| WO | WO 2019/145762 | 8/2019 |

OTHER PUBLICATIONS

Baby Quasar—Quasar BioTech—LED Light Therapy Tools, https://www.web.archive.org/web/20180822083757/https://babyquasar.com/, dated Aug. 22, 2018, accessed on Oct. 7, 2019.

Beauty Star RF Cavitation Ultrasonic Slimming Massager LED Fat Burner Anti Cellulite Lipo Device Skin Tightening Weight Loss Beauty Machine, http://www.stresslesshomes.co.uk/RF-Cavitation-Ultrasonic-Slimming-Massager-LED-Fat-Burner-Anti-Cellulite-Lipo-Device-Skin-Tightening-Weight-Loss-Beauty-Machine-p-4808.html, accessed Aug. 20, 2019.

BEYONTH 4 in 1 RF Radio Frequency Ultrasonic Ultrasuond EMS Photon Vibration Led Light Skin Tighten Facial Care Massager, BEYONTH Authorized Store, https://www.aliexpress.com/item/32612318052.html, accessed Aug. 21, 2019.

Comper Smarkin, Comper Healthcare, https://web.archive.org/web/20181122200114/https://www.comper.com/en/meirong.html, dated Nov. 22, 2018, accessed on Oct. 7, 2019.

Dr. Arrivo Ghost, https://web.archive.org/web/20180830110419/http://artistic-onlineshop.com/page_13.html, dated Aug. 30, 2018, accessed on Oct. 7, 2019.

Dr. Arrivo The Zeus, https://web.archive.org/web/20180830110810/http://artistic-onlineshop.com/page_10.html, dated Aug. 30, 2018, accessed on Oct. 7, 2019.

FOREO UFO, https://web.archive.org/web/20180109225036/https://www.kickstarter.com/projects/17/3400091/ufo-beauty-tech-revolutionizes-face-masks-in-90-se/description, dated Jan. 9, 2018, accessed on Oct. 7, 2019.

Galvanic Spa®, NuSkin®, https://web.archive.org/web/20160220092834/http://www.amazon.com/GALVANIC-ageLOC-Spa-Package-System/dp/B000SU7W58, dated Feb. 20, 2016, accessed on Oct. 7, 2019.

Hitachi CM-N810-P, HADA CRIE Facial Moisturizer Massager AC100-240V, https://web.archive.org/web/20160304055951/https://wwww.amazon.com/Hitachi-CM-N810-P-Moisturizer-Massager-AC100-240V/dp/B0050X3FEA, dated Mar. 4, 2016, accessed on Oct. 7, 2019.

JeNu Ultrasonic Infuser with 2 Microsphere Conducting Gels, https://web.archive.org/web/20160305235441/https://www.qvc.com/JeNu-Ultrasonic-Infuser-with-2-Microsphere-Conducting-Gels.productA272293.html, dated Mar. 5, 2016, accessed on Oct. 7, 2019.

LightStim for Wrinkles, https://www.lightstim.com/wrinkles, dated Jan. 28, 2017, access on Oct. 7, 2019.

Microcurrent Facial Lifting and Toning Devices—NuFACE, https://web.archive.org/web/20150109190647/https://www.mynuface.com/, dated Jan. 9, 2015, accessed on Oct. 8, 2019.

Mirang Co., Ltd., https://web.archive.org/web/20171021062732/http://en.mirang.kr/, dated Oct. 21, 2017, accessed on Oct. 8, 2019.

Nanotime Beauty, NanoSkin smart Skin Tendering Apparatus, https://web.archive.org/web/20180602161209/http://nt-beauty.com/nanocute_en.html, dated Jun. 2, 2018, accessed on Oct. 7, 2019.

NEWA—Beauty Device for Home Use, Anti Aging Device with Addons, https://web.archive.org/web/20171116233415/https://newbeauty.com/, dated Nov. 16, 2017, accessed on Oct. 7, 2019.

Perfectio by Zero Gravity, https://web.archive.org/web/20180818202214/https://www.zerogravityskin.com/, dated Aug. 18, 2018, accessed on Oct. 7, 2019.

Shrih Mini Rf LED Wrinkle Removal Anti Aging Skin Lifting Massager, http://shopping.rediff.com/product/shrih-mini-rf-led-wrinkle-removal-anti-aging-skin-lifting-massager/20346093, accessed Aug. 20, 2019.

Skin Inc., Skin Supplement Bar, https://web.archive.org/seb/20180909150539/https://www.iloveskininc.com/, dated Sep. 9, 2018, accessed on Oct. 7, 2019.

Titan Anti-Aging Facial Skin Lifting & Tightening, https://web.archive.org/web/20170928192405/https://silkn.com/collections/frontpage/products/titan-skin-tightening?variant=40530480074, dated Sep. 28, 2017, accessed on Oct. 7, 2019.

Tripollar, Pollogen, Medical devices for aesthetic professionals, https://web.archive.org/web/20181103223431/http://www.pollogen.com/pollogen-products.html, dated Nov. 3, 2018, accessed on Oct. 7, 2019.

Yaman RF Facial Lifting, https://web.archive.org/web/20180918151203/https://www.yohohongkong.com/en_us/product/1875-Yaman-RF-EX-HRF-3-Facial-Lifiting-and-Moisturizing-Device, dated Sep. 18, 2018, accessed on Oct. 7, 2019.

ZIIP Beauty, https://web.archive.org/web/2017121065233/https://ziipbeauty.com/, dated Dec. 10, 2017, access on Oct. 7, 2019.

SKIN TREATMENT DEVICE

INCORPORATION BY REFERENCE TO ANY PRIORITY APPLICATIONS

This application claims the benefit of U.S. Provisional Application No. 62/789,537, filed Jan. 8, 2019, titled "6 IN 1 AT HOME BEAUTY DEVICE (LED, ULTRASOUND, EMS, RF, ION INFUSION, SONIC PULSATIONS)," which is hereby incorporated by reference in its entirety. Any and all applications for which a foreign or domestic priority claim is identified in the Application Data Sheet as filed with the present application are hereby incorporated by reference under 37 CFR 1.57.

BACKGROUND

Today, many different types of skincare devices are available for applying skincare treatments such as removing wrinkles, infusing nutrients, and detoxifying the skin. These skincare devices are used not only at professional skincare shops, but also at home by many consumers, due to their easy-to-use nature.

SUMMARY

Provided is a skincare device for providing skincare treatments to a user's skin. The skincare device has a body that includes a body having a skin-contacting surface, an ultrasound probe configured to generate ultrasound waves, radio frequency electrodes configured to generate radio frequency waves, electrical stimulation electrodes configured to generate electrical impulses and negative ions, light emitting diodes configured to emit light, and circuitry housed in the body and comprising at least one processor and at least one memory. The ultrasound probe, the radio frequency electrodes, and the electrical stimulation electrodes may collectively be referred to herein as "skincare electrodes." The skincare electrodes can be arranged such that all of the skincare electrodes are configured to contact the user's skin simultaneously. The skincare electrodes may be shaped and arranged such that contact between the skincare electrodes and the user's skin or the treatment effect is improved (e.g., as the skincare device is moved across an area on the user's skin). The skincare device may have a plurality of treatment modes in which different combinations of these skincare electrodes and the light emitting diodes are activated.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which.

DETAILED DESCRIPTION OF EMBODIMENTS

Embodiments of the invention will now be described with reference to the accompanying figures. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

Introduction

Today, many skincare devices are available for applying various treatments on their users' skin. The present disclosure provides techniques for improving the application of these and other treatments using unique arrangements of skin-contacting electrodes and unique combinations of technologies.

Skincare Device

Figure 1:
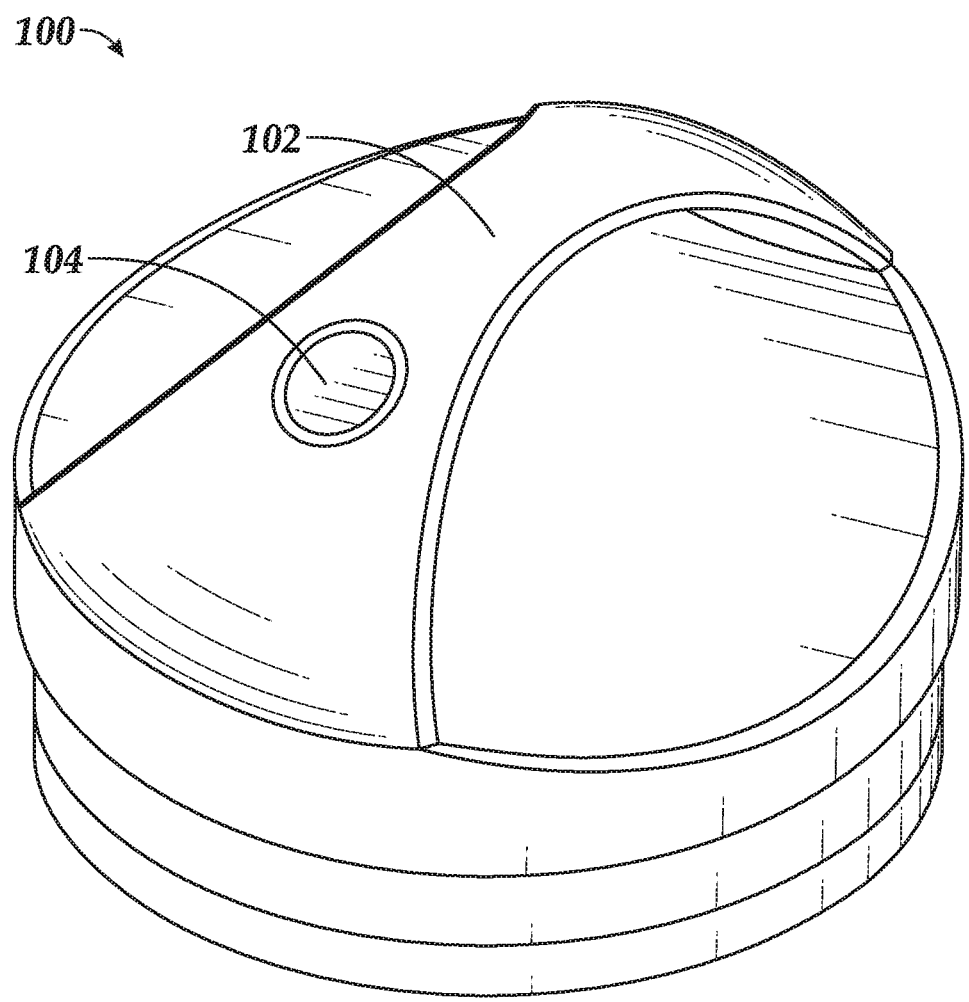
FIG. 1 illustrates a perspective view of a skincare device, according to an example embodiment.

FIG. 1 illustrates a skincare device 100. As shown in FIG. 1, the skincare device 100 includes a handle 102 for holding the skincare device 100 and a function key 104 for turning the skincare device 100 on and off and for toggling through the treatment modes of the skincare device 100. In some embodiments, the handle 102 includes one or more electrodes (e.g., on a side that is facing the body of the skincare device 100 in FIG. 1) connected to one or more of the skincare electrodes described in greater detail below with reference to FIGS. 2A, 2B, 3, and 4. A user may turn on the skincare device 100 by pressing the function key 104 (e.g., a long press), toggle through the series of treatment modes of the skincare device 100 by pressing the function key 104 (e.g., short presses), and turn off the skincare device 100 by pressing the function key 104 again (e.g., a long press). While any of the treatment modes (along with the corresponding skincare electrodes and/or LEDs) are active, the user can bring the bottom surface (also referred to herein as the skin-contacting surface) of the skincare device 100 (e.g., the surface on which the skincare device 100 is resting in FIG. 1) in contact with the user's skin, and slide the skincare device 100 across an area on the user's skin while maintaining the contact between the skin-contacting surface of the skincare device 100 and the user's skin. The various treatment modes of the skincare device 100 are described in greater detail below with reference to FIGS. 3 and 4.

Skin-Contacting Surface

Figure 2A:
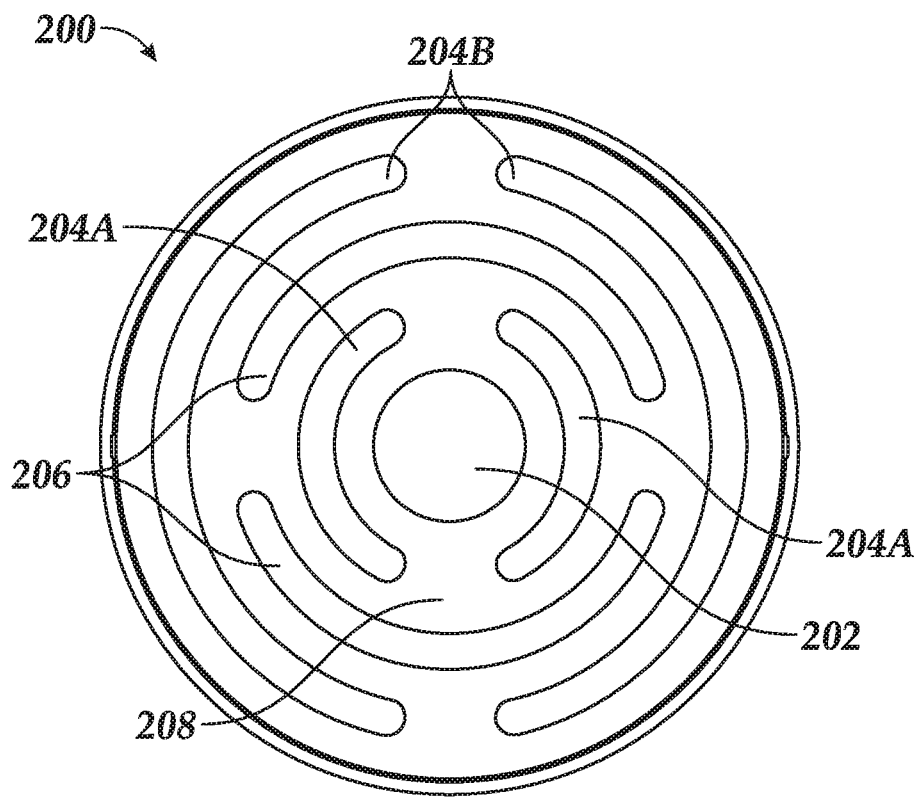
FIG. 2A illustrates a bottom view of a skincare device, according to an example embodiment.
Figure 2B:
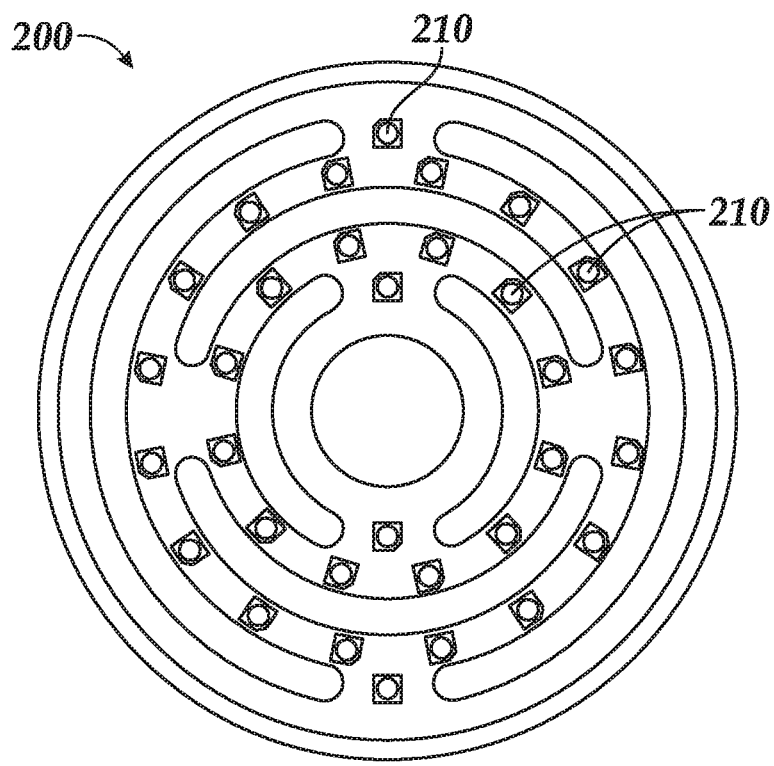
FIG. 2B illustrates another bottom view of a skincare device, according to an example embodiment.

FIGS. 2A and 2B illustrate a view of the skin-contacting surface 200 of the skincare device 100 shown in FIG. 1. As shown in FIG. 2A, the skin-contacting surface 200 includes an ultrasound probe 202, electrical muscle stimulation (EMS) and ion infusion electrodes 204, radio frequency (RF) electrodes 206, and a translucent cover 208. As shown in FIG. 2B, underneath the translucent cover 208, light emitting diodes (LEDs) 210 are provided. When the LEDs 210 are on, the translucent cover 208 allows the light emitted by the LEDs 210 through such that the user of the skincare device 100 can see the color of the light emitted by the LEDs 210. For example, the color of the light emitted by the LEDs 210 can be one of red, green, and blue. The translucent cover 208 may be made of an electrically insulating material.

Arrangement of Ultrasound Probe

The ultrasound probe 202 is configured to generate ultrasound waves. As shown in FIG. 2A, the ultrasound probe 202 has a round shape and is positioned in a central portion of the skin-contacting surface 200.

Arrangement of Inner EMS and Ion Infusion Electrodes

The EMS and ion infusion electrodes 204A and 204B are configured to generate electrical impulses and negative ions. The EMS and ion infusion electrodes 204 include first electrodes 204A (the inner two) and second electrodes 204B (the outer two). As shown in FIG. 2A, each of the first electrodes 204A is elongated and curved around the ultrasound probe 202, and the first electrodes 204A are separated from each other by two or more gaps ("first gaps") and further separated from the ultrasound probe 202 by the translucent cover 208.

Arrangement of Radio Frequency Electrodes

The radio frequency electrodes 206 are configured to generate radio frequency waves. As shown in FIG. 2A, each of the radio frequency electrodes 206 is elongated and curved around the ultrasound probe 202 and the first electrodes 204A. The radio frequency electrodes are (i) separated from each other by two or more gaps ("second gaps") that are not aligned with any of the two or more first gaps (e.g., between the nearest ends of the first electrodes 204A) along a radial direction from the ultrasound probe 202 and (ii) further separated from the first electrodes 204A by the translucent cover 208. As shown in FIG. 2A, the first gaps (e.g., between the nearest ends of the first electrodes 204A) face upward and downward relative to the ultrasound probe 202, and the second gaps (e.g., between the nearest ends of the radio frequency electrodes 206) face left and right relative to the ultrasound probe 202.

Technical Advantages of Non-Aligned Gaps

By providing non-aligned gaps between skincare electrodes (e.g., first gaps and second gaps described above), contact between the skincare electrodes and the user's skin can be made more consistent and less dependent on the direction in which the skincare device 100 is moved across the user's skin. For example, if all of the gaps were aligned along a direction, and the user moves the skincare device 100 across the user's face in the same direction, the portions of the user's skin along that direction may receive minimal or reduced contact with the skincare electrodes, which may reduce the effectiveness of the skin treatments provided by the skincare device 100. By ensuring that at least one of the electrodes (or at least one of the imaginary concentric rings on the skin-contacting surface 200) does not have a gap along the same direction, contact between the skincare electrodes and the user's skin can be made increased for such portions of the user's skin along that direction.

However, in some embodiments, all of the gaps between the nearest two ends of the skincare electrodes are aligned (e.g., arranged in a straight line that passes through the center of the skin-contacting surface 200). In other embodiments, each of the gaps between the nearest two ends of the skincare electrodes is aligned with at least one other gap such that such gaps are arranged on the same radial segment from the center of the skin-contacting surface 200 to the edge of the skin-contacting surface 200). In other embodiments, each of the gaps between the nearest two ends of the skincare electrodes and positioned on a given imaginary concentric ring of a plurality of imaginary concentric rings of skincare electrodes on the skin-contacting surface 200, is aligned with another gap from each of the remaining imaginary concentric rings of the plurality of imaginary concentric rings of skincare electrodes such that such gaps are arranged on the same radial segment from the center of the skin-contacting surface 200 to the edge of the skin-contacting surface 200).

Arrangement of Outer EMS and Ion Infusion Electrodes

As shown in FIG. 2A, each of the second electrodes 204B is elongated and curved around the ultrasound probe 202, the first electrodes 204A, and the radio frequency electrodes 206. Further, the second electrodes 204B are separated from each other and further separated from the radio frequency electrodes by the translucent cover 208.

Further, as shown in FIG. 2A, the second electrodes 204B are separated from each other by two or more gaps ("third gaps") that are (i) aligned with the first gaps (e.g., between the nearest ends of the first electrodes 204A) along a radial direction from the ultrasound probe 202, and (ii) not aligned with any of the second gaps (e.g., between the nearest ends of the radio frequency electrodes 206) along a radial direction from the ultrasound probe 202. As shown in FIG. 2A, the first gaps (e.g., between the nearest ends of the first electrodes 204A) face upward and downward relative to the ultrasound probe 202, the second gaps (e.g., between the nearest ends of the radio frequency electrodes 206) face left and right relative to the ultrasound probe 202, and the third gaps (e.g., between the nearest ends of the second electrodes 204B) face upward and downward relative to the ultrasound probe 202 (therefore aligned with the first gaps).

Arrangement of Light Emitting Diodes

The light emitting diodes 210 are configured to emit light. The light emitting diodes 210 are located between two adjacent ones of the skincare electrodes (e.g., ultrasound probe 202, first electrodes 204A, radio frequency electrodes 206, and second electrodes 204B) and underneath the translucent cover 208 (e.g., electrically insulating material separating the skincare electrodes). In some embodiments, one or more light emitting diodes are placed in each one of the first gaps. In some embodiments, one or more light emitting diodes are placed in each one of the second gaps. In some embodiments, one or more light emitting diodes are placed in each one of the third gaps. In some embodiments, none light emitting diode is placed in any of the first gaps. In some embodiments, none light emitting diode is placed in any of the second gaps. In some embodiments, none light emitting diode is placed in any of the third gaps. In some embodiments, the light emitting diodes placed in the first gaps and the third gaps are aligned.

Arrangement of Skincare Electrodes in Imaginary Concentric Rings

In some embodiments, the first electrodes 204A form portions of a first imaginary concentric ring of a plurality of imaginary concentric rings around the ultrasound probe 202, the radio frequency electrodes 206 form portions of a second imaginary concentric ring of the plurality of imaginary concentric rings around the ultrasound probe 202, and the second electrodes 204B form portions of a third imaginary concentric ring of the plurality of imaginary concentric rings around the ultrasound probe 202. In some of such embodiments, each of the first electrodes 204A spans less than half of the first imaginary concentric ring but more than quarter of the first imaginary concentric ring. Similarly, each of the radio frequency electrodes 206 may span less than half of the second imaginary concentric ring but more than quarter of the second imaginary concentric ring. Similarly, each of the second electrodes 204B may span less than half of the third imaginary concentric ring but more than quarter of the third imaginary concentric ring.

Further, the shortest distance between the first imaginary concentric ring and the second imaginary concentric ring may be equal to a shortest distance between the second imaginary concentric ring and the third imaginary concentric ring. In some cases, each of the radio frequency electrodes 206 may be longer than any of the first electrodes 204A. Further, each of the second electrodes 204B may be longer than any of the radio frequency electrodes 206.

Technical Advantages of Skincare Electrodes Arranged on Concentric Rings

By providing a plurality of skincare electrodes that each cover only a portion of an imaginary concentric ring on the skin-contacting surface (e.g., rather than being a full ring), the skincare device 100 is configured to provide mode dynamic skincare treatments by applying different types, polarities, and/or levels of waves, vibrations, electrical pulses, stimulations, and the like. For example, in some embodiments, the electrodes of any one of the given imaginary concentric rings may have different types, polarities, and/or levels of waves, vibrations, electrical pulses, or stimulations. In other embodiments, the electrodes of any one of the given imaginary concentric rings may have the same type, polarity, and/or level of waves, vibrations, electrical pulses, or stimulations. However, in some embodiments, one or more (or all) of the skincare electrodes provided on the skin-contacting surface 200 are full rings instead.

Additional Skincare Electrodes

Although the example of FIG. 2A shows two first electrodes 204A, two radio frequency electrodes 206, and two second electrodes 204B, any other number of electrodes for any of the imaginary concentric rings. Additionally or alternatively, the skin-contacting surface 200 may include any number of imaginary concentric rings (2, 3, 4, 5, etc.).

Flowchart for Operating Skincare Device

Figure 3:
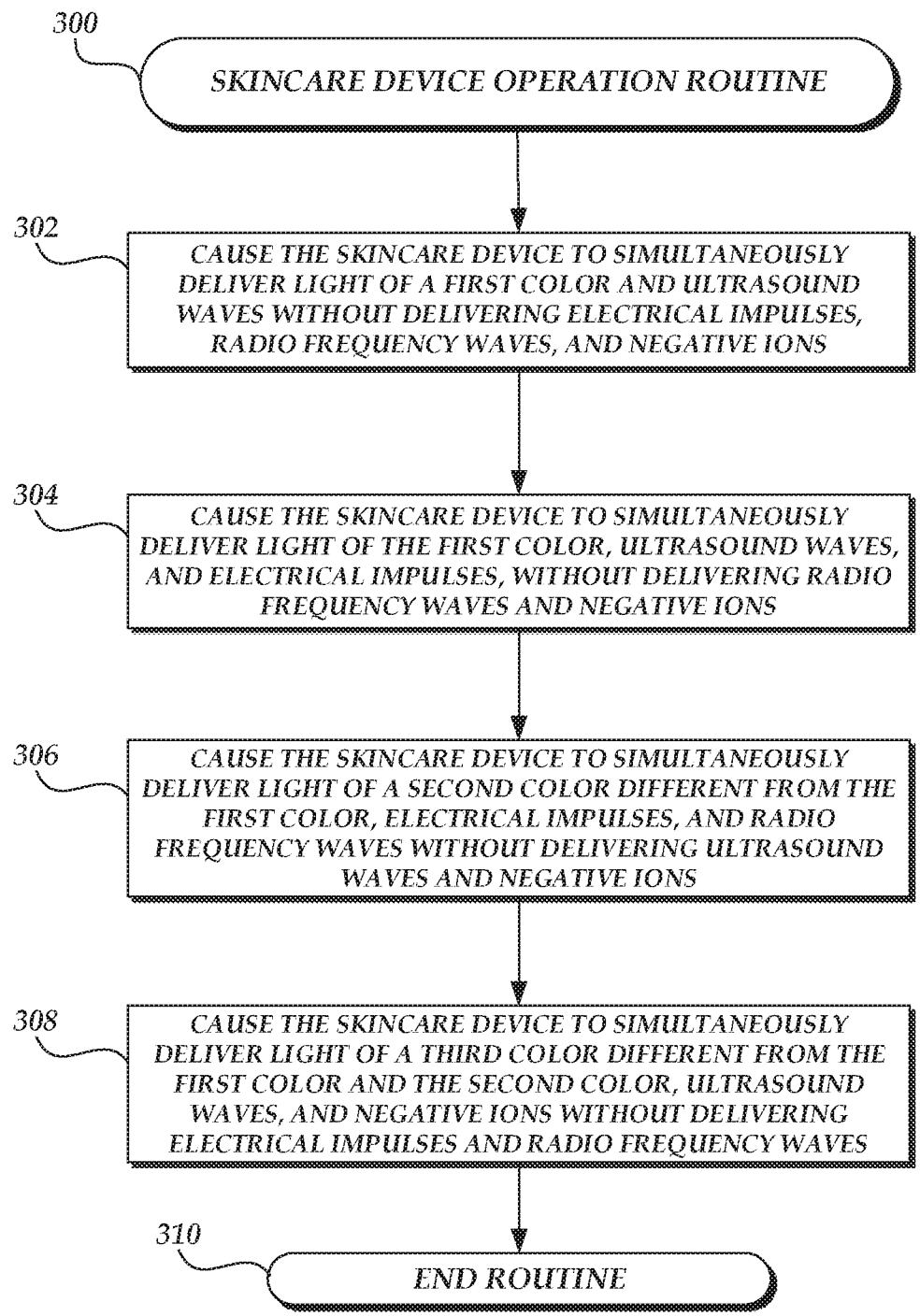
FIG. 3 illustrates a flowchart depicting a method for operating a skincare device, according to an example embodiment.

FIG. 3 is a flowchart for operating the skincare device, according to an embodiment of the present invention. The steps illustrated in FIG. 3 may be performed by the microcontroller unit 414 of FIG. 4 described below, or any other components of the skincare device 100 of FIG. 1 or the skincare device 400 of FIG. 4. For convenience, the method 300 is described as performed by the microcontroller unit 414.

First Treatment Mode (Detox)

At block 302, the microcontroller unit 414 causes the skincare device to simultaneously deliver light of a first color and ultrasound waves without delivering electrical impulses, radio frequency waves, and negative ions.

Second Treatment Mode (Tone)

At block 304, the microcontroller unit 414 causes the skincare device to simultaneously deliver light of the first color, ultrasound waves, and electrical impulses, without delivering radio frequency waves and negative ions. For example, the microcontroller unit 414 causes the skincare device to do so in response to detecting user activation of a button while the skincare device is in a treatment mode in which light of the first color and ultrasound waves are delivered, without delivering electrical impulses, radio frequency waves, and negative ions (e.g., first treatment mode).

Third Treatment Mode (Lift)

At block 306, the microcontroller unit 414 causes the skincare device to simultaneously deliver light of a second color different from the first color, electrical impulses, and radio frequency waves without delivering ultrasound waves and negative ions. For example, the microcontroller unit 414 causes the skincare device to do so in response to detecting user activation of a button while the skincare device is in a treatment mode in which light of the first color, ultrasound waves, and electrical impulses are delivered, without delivering radio frequency waves and negative ions (e.g., second treatment mode).

Fourth Treatment Mode (Infuse)

At block 308, the microcontroller unit 414 causes the skincare device to simultaneously deliver light of a third color different from the first color and the second color, ultrasound waves, and negative ions without delivering electrical impulses and radio frequency waves. For example, the microcontroller unit 414 causes the skincare device to do so in response to detecting user activation of a button while the skincare device is in a treatment mode in which light of the second color different from the first color, electrical impulses, and radio frequency waves are delivered, without delivering ultrasound waves and negative ions (e.g., third treatment mode).

Returning to First Treatment Mode (Detox)

The microcontroller unit 414 may cause the skincare device to transition to the first treatment mode in response to detecting user activation of a button while the skincare device is in a treatment mode in which light of the third color different from the first color and the second color, ultrasound waves, and negative ions are delivered, without delivering electrical impulses and radio frequency waves (e.g., fourth treatment mode).

Variations

In the method 300, one or more of the blocks shown in FIG. 3 may be removed (e.g., not performed) and/or the order in which the method is performed may be switched. In some embodiments, additional blocks may be added to the method 300. Thus, the embodiments of the present disclosure are not limited to or by the example shown in FIG. 3, and other variations may be implemented without departing from the spirit of this disclosure.

Example Architecture of Skincare Device

Figure 4:
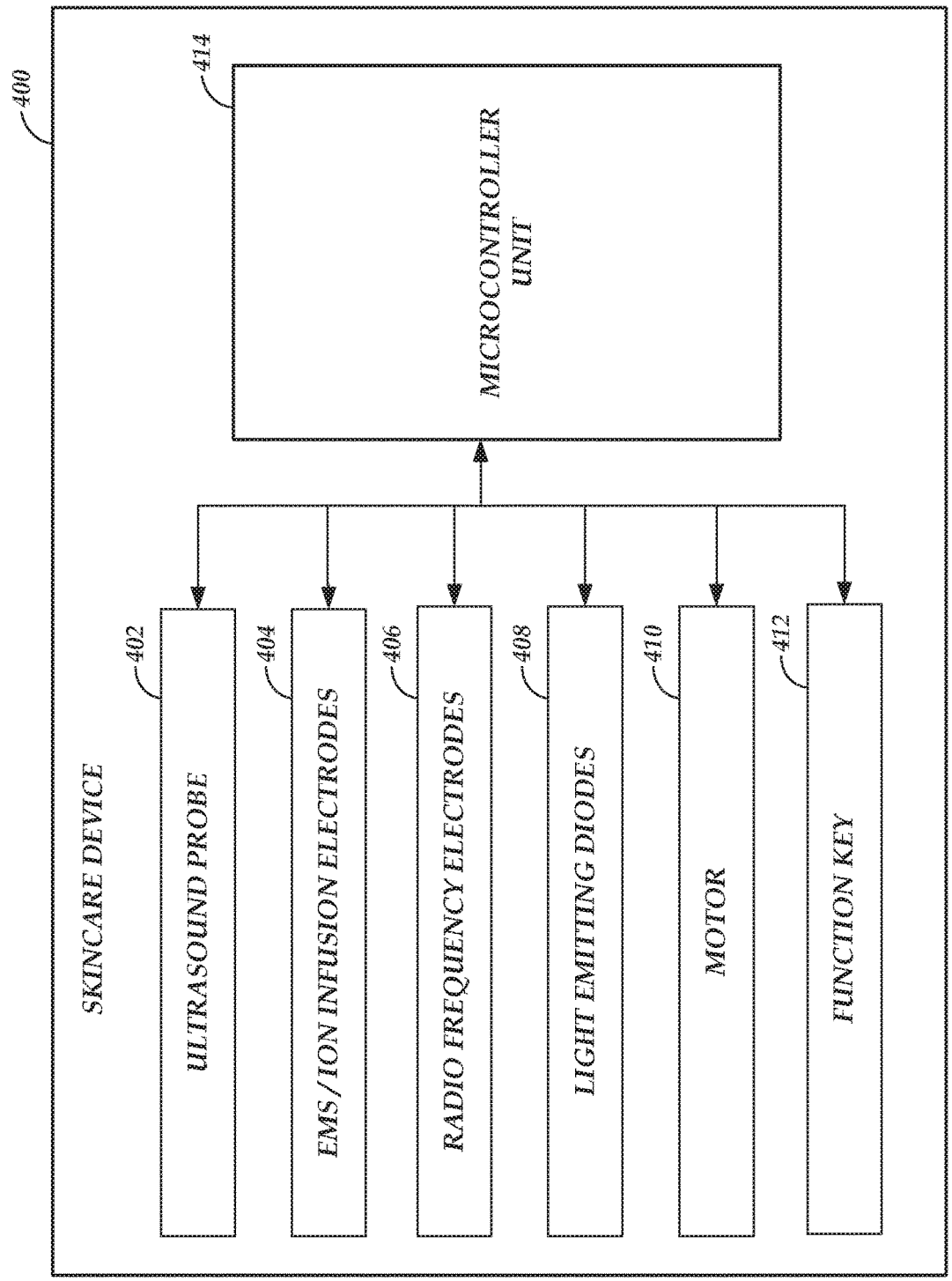
FIG. 4 illustrates a block diagram of a skincare device, according to an example embodiment.

FIG. 4 illustrates a block diagram of a skincare device 400, according to an example embodiment. As shown in FIG. 4, the skincare device 400 includes an ultrasound probe 402, EMS and ion infusion electrodes 404, radio frequency electrodes 406, light emitting diodes 408, a motor 410, and a function key 412, all of which are in communication with a microcontroller unit 414.

Ultrasound Probe

The ultrasound probe 402 is configured to generate ultrasound waves. For example, the ultrasound probe 402 uses ultrasound waves to penetrate the skin's surface to renew, repair, tone, increase blood circulation, lymphatic drainage, combat swelling, and properly prepare the skin for product absorption. In one embodiment, the ultrasound probe 402 uses 3 MHz sound waves. This technique may result in one or more of the following health benefits: leave you refreshed, brighter, lifted, and toned, detox skin, improve skin texture and tone, enhance skin care product performance, increase cell metabolism, refine large pores, aid in lymphatic drainage, and stimulate blood circulation. Ultrasound waves enter the body and are absorbed by the muscles. This may increase the temperature of surrounding tissue, thereby increasing circulation, oxygen absorption, and removal of wastes.

EMS and Ion Infusion Electrodes

The EMS and ion infusion electrodes 404 are configured to generate electrical impulses and negative ions. For example, the EMS and ion infusion electrodes 404 use electrical currents to stimulate specific muscles underneath the user's skin. This technique may result in one or more of the following health benefits: fight signs of aging, rejuvenate aging, wrinkled, and sagging skin, increase circulation, reduce swelling, smoother complexion, and tone, firm, and strengthen muscle.

Additionally, the EMS and ion infusion electrodes 404 use charged galvanic currents to improve penetration and delivery of age combating ingredients (antioxidants, vitamins, peptides, and active ingredients) beyond the superficial layer of the user's skin. This technique may result in one or more of the following health benefits: regenerate the skin, tighten and firm tissues, calm and soothe the skin, reduce swelling, increase circulation, restore moisture, oxygenate cells, stimulate cell renewal, and improve skin's overall vitality.

Although described herein as being configured to output electrical impulses (EMS mode), negative ions (ion infusion mode), or neither (off mode), in some embodiments, the EMS and ion infusion electrodes 404 are EMS electrodes configured to output electrical impulses and not configured to output negative ions. In other embodiments, the EMS and ion infusion electrodes 404 are ion infusion electrodes configured to output negative ions and not configured to output electrical impulses.

Radio Frequency Electrodes

The radio frequency electrodes 406 are configured to generate radio frequency (RF) waves. RF waves deliver heat and energy to deeper levels of the user's skin. The heat stimulates a healing response from the brain and triggers: tightening of collagen fibers (the immediate contraction of fibers is results in a "tightening" effect); and production of collagen (stimulating collagen producing cells). In addition to producing collagen and elastin to tighten, contour, and lift the skin, RF waves also stimulate oxygen production, thereby brightening and rejuvenating the skin.

Light Emitting Diodes

The light emitting diodes 408 are configured to emit light. The light emitting diodes 408 may emit one of red light, green light, and blue light. The light emitting diodes 408 are configured to emit light deep into the skin in various therapeutic wavelengths and spectrums to trigger intracellular reactions. In the correct wavelengths, LED lights stimulate sensors in the skin to boost cellular activity. For example, the light emitted by the light emitting diodes 408 can help fibroblast cells in the user's dermal layer produce more collagen and elastin. Collagen provides the skin fullness, and elastin provides the skin the ability to bounce back. LED light aids the skin by acting as fuel for the cells. Our body converts the light energy into ATP (adenosine triphosphate), or energy used by cells. After treatment, fibroblast cells have a full tank of fuel to produce more collagen and elastin.

The user's skin may respond differently depending on the type of light being emitted. For example, red light (e.g., about 640 nm, or 635-700 nm) can: tighten and reduce fine line and wrinkles by building, strengthening, and maximizing cellular structure, reduce inflammation and redness by decreasing the amount of cytokines, and plump the skin, target water layers on elastin, thereby reducing appearance of wrinkles. As another example, blue light (e.g., about 460 nm, or 450-490 nm) can fight acne by producing oxygen radicals that kill *Propionibacterium acnes*, a bacteria responsible for acne. As another example, green light (e.g., about 525 nm, or 520-560 nm) can: correct hyperpigmentation and even out skin tone by breaking up melanin (responsible for age spots and pigmentation) and preventing it from traveling to the skin's surface to diminish existing discoloration, and prevent hyperpigmentation by inhibiting excess production of melanin.

Motor

The motor 410, when activated, causes the skincare device 400 to vibrate. In some embodiments, the motor 410 is activated in one or more treatment modes in which the ultrasound probe 402 is activated, and is deactivated in one or more treatment modes in which the ultrasound probe 402 is deactivated. In some embodiments, the motor 410 is activated in one or more treatment modes in which the radio frequency electrodes 406 are deactivated, and is deactivated in one or more treatment modes in which the radio frequency electrodes 406 are activated. In some embodiments, the motor 410 is activated in one or more treatment modes in which the light emitting diodes 408 emit light of a specific color (e.g., red, green, or blue), and is deactivated in one or more treatment modes in which the light emitting diodes 408 emit light of the specific color. In some embodiments, the motor 410 is activated in one or more treatment modes in which a specific one of the ultrasound probe 402, the EMS and ion infusion electrodes 404, the radio frequency electrodes 406, the light emitting diodes 408, and the motor 410 is activated, and is deactivated in one or more treatment modes in which the specific one of the ultrasound probe 402, the EMS and ion infusion electrodes 404, the radio frequency electrodes 406, the light emitting diodes 408, and the motor 410 is deactivated. In some embodiments, the motor 410 is activated in one or more treatment modes in which a specific one of the ultrasound probe 402, the EMS and ion infusion electrodes 404, the radio frequency electrodes 406, the light emitting diodes 408, and the motor 410 is deactivated, and is deactivated in one or more treatment modes in which the specific one of the ultrasound probe 402, the EMS and ion infusion electrodes 404, the radio frequency electrodes 406, the light emitting diodes 408, and the motor 410 is activated.

Function Key

The function key 412 may be a physical button or a digital button (e.g., which can be activated by a physical press or a touch). Although a single function key is shown in FIG. 4, the function key 412 may be split into multiple keys or buttons. For example, there may be a power button for turning the skincare device 400 on and off, and there may be a separate button for toggling through the one or more treatment modes. In some embodiments, each mode has a separate button for selecting the mode. In other embodiments, the function key 412 is the only button that is used to power on and off the skincare device 400 and also select one or more of the treatment modes.

Microcontroller Unit

The microcontroller unit 414 comprises circuitry housed in the body of the skincare device 400 and configured to activate or deactivate any combination of the ultrasound probe 402, the EMS and ion infusion electrodes 404, the radio frequency electrodes 406, the light emitting diodes 408, and the motor 410 depending on the current operating mode of the skincare device 400. The microcontroller unit 414 may include one or more hardware processors and one or more memories and/or circuit elements for storing computer-executable instructions and/or other types of information.

Transitioning to First Treatment Mode

In response to a user activation of the function key 412 (e.g., in an off state or in a fourth treatment mode), the microcontroller unit 414 may, in a first treatment mode, cause the skincare device 400 to simultaneously deliver blue and ultrasound waves without delivering electrical impulses, radio frequency waves, and negative ions.

Transitioning to Second Treatment Mode

In response to another user activation of the function key 412 (e.g., in the first treatment mode), the microcontroller unit 414 may, in a second treatment mode, cause the skincare device 400 to simultaneously deliver blue light, ultrasound waves, and electrical impulses, without delivering radio frequency waves and negative ions.

Transitioning to Third Treatment Mode

In response to another user activation of the function key 412 (e.g., in the second treatment mode), the microcontroller unit 414 may, in a third treatment mode, cause the skincare device 400 to simultaneously deliver red light, electrical impulses, and radio frequency waves without delivering ultrasound waves and negative ions.

Transitioning to Fourth Treatment Mode

In response to another user activation of the function key 412 (e.g., in the third treatment mode), the microcontroller unit 414 may, in a fourth treatment mode, cause the skincare device 400 to simultaneously deliver green light, ultrasound waves, and negative ions without delivering electrical impulses and radio frequency waves.

Transitioning to First Treatment Mode

In response to another user activation of the function key 412 (e.g., in the fourth treatment mode), the microcontroller unit 414 may cause the skincare device 400 to return to the first treatment mode, in which the microcontroller unit 414 may cause the skincare device 400 to simultaneously deliver blue and ultrasound waves without delivering electrical impulses, radio frequency waves, and negative ions.

Other Variations on Controlling Skincare Device

Although the four treatment modes are described above with reference to the microcontroller unit 414, in some embodiments, the microcontroller unit 414 may cause, in other modes, other combinations of the ultrasound probe 402, the EMS and ion infusion electrodes 404, the radio frequency electrodes 406, the light emitting diodes 408, and the motor 410 to be activated. In addition, although the specific order in which the treatment modes are transitioned is described above with reference to the microcontroller unit 414, the treatment modes may be transitioned in any one of all permutations of the transitioning order (e.g., first to third, third to second, second to fourth, or any mode N to mode M, where N and M are different integers that uniquely identify the two modes).

Using Skincare Device

The user of the skincare device 400 can activate the first treatment mode by pressing a button (e.g., the function key 412). The user may then move the skincare device 400 across an area on the user's skin while the skin-contacting surface 200 of the skincare device 400 is touching the user's skin and while the skincare device 400 is in the first treatment mode. When the user is done, the user can cause the skincare device 400 to transition from the first treatment mode to the second treatment mode by pressing the button. The user may move the skincare device 400 across an area on the user's skin while the skin-contacting surface 200 of the skincare device 400 is touching the user's skin and while the skincare device 400 is in the second treatment mode. Then, the user can cause the skincare device 400 to transition from the second treatment mode to the third treatment mode by pressing the button. The user may move the skincare device 400 across the area on the user's skin while the skin-contacting surface 200 of the skincare device 400 is touching the user's skin and while the skincare device 400 is in the third treatment mode. Then, the user can cause the skincare device 400 to transition from the third treatment mode to the fourth treatment mode by pressing the button. The user may move the skincare device 400 across the area on the user's skin while the skin-contacting surface 200 of the skincare device 400 is touching the user's skin and while the skincare device 400 is in the fourth treatment mode. Then, the user can cause the skincare device 400 to transition from the fourth treatment mode to the first treatment mode by pressing the button (e.g., short press). While the skincare device 400 is in the fourth treatment mode, the user may turn off the skincare device 400 by pressing the button without causing the skincare device 400 to transition to the first treatment mode (e.g., long press).

Additional Example Embodiments (EEs)

Some examples of embodiments of the present disclosure are provided in this section in the form of devices and methods, without limitation.

EE 1: A skincare device, comprising: a body having a skin-contacting surface configured to contact a user's skin; an ultrasound probe configured to generate ultrasound waves; a plurality of radio frequency electrodes configured to generate radio frequency waves; a plurality of electrical stimulation electrodes configured to generate electrical impulses and negative ions, the plurality of electrical stimulation electrodes comprising two or more first electrical stimulation electrodes and two or more second electrical stimulation electrodes; a plurality of light emitting diodes configured to emit light; circuitry housed in the body and comprising at least one processor and at least one memory; wherein the ultrasound probe, the plurality of radio frequency electrodes, and the plurality of electrical stimulation electrodes are collectively referred to as skincare electrodes, wherein the skincare electrodes and the plurality of light emitting diodes are arranged to provide the skin-contacting surface in which (1) the ultrasound probe is positioned in a central portion of the skin-contacting surface, (2) each of the two or more first electrical stimulation electrodes is elongated and curved around the ultrasound probe, (3) the two or more first electrical stimulation electrodes are separated from each other by two or more first gaps and further separated from the ultrasound probe by an electrically insulating material, (4) each of the plurality of radio frequency electrodes is elongated and curved around the ultrasound probe and the two or more first electrical stimulation electrodes, (5) the plurality of radio frequency electrodes are (i) separated from each other by two or more second gaps that are not aligned with any of the two or more first gaps along a radial direction from the ultrasound probe and (ii) further separated from the two or more first electrical stimulation electrodes by the electrically insulating material, (6) each of the two or more second electrical stimulation electrodes is elongated and curved around the ultrasound probe, the two or more first electrical stimulation electrodes, and the plurality of radio frequency electrodes, (7) the two or more second electrical stimulation electrodes are separated from each other and further separated from the plurality of radio frequency electrodes by the electrically insulating material, and (8) the plurality of light emitting diodes are located between two adjacent ones of the skincare electrodes and underneath the electrically insulating material separating the skincare electrodes, such that all of the skincare electrodes are configured to simultaneously contact the user's skin and the plurality of light emitting diodes are configured to deliver light to the user's skin through the electrically insulating material to apply a plurality of skincare treatments to the user's skin using the plurality of light emitting diodes and at least part of the skincare electrodes, wherein the at least one processor is programmed to activate a plurality of skincare treatment modes corresponding to the plurality of skincare treatments, the plurality of skincare treatment modes comprising a first treatment mode, a second treatment mode, a third treatment mode, and a fourth treatment mode, wherein (i) in the first treatment mode, the at least one processor causes the skincare device to simultaneously deliver light of a first color and ultrasound waves without delivering electrical impulses, radio frequency waves, and negative ions, (ii) in the second treatment mode, the at least one processor causes the skincare device to simultaneously deliver light of the first color, ultrasound waves, and electrical impulses, without delivering radio frequency waves and negative ions, (iii) in the third treatment mode, the at least one processor causes the skincare device to simultaneously deliver light of a second color different from the first color, electrical impulses, and radio frequency waves without delivering ultrasound waves and negative ions, and (iv) in the fourth treatment mode, the at least one processor causes the skincare device configured to simultaneously deliver light of a third color different from the first color and the second color, ultrasound waves, and negative ions without delivering electrical impulses and radio frequency waves.

EE 2: The skincare device of EE 1, wherein the two or more first electrical stimulation electrodes form portions of a first imaginary concentric ring of a plurality of imaginary concentric rings around the ultrasound probe, the plurality of radio frequency electrodes form portions of a second imaginary concentric ring of the plurality of imaginary concentric rings around the ultrasound probe, and the two or more second electrical stimulation electrodes form portions of a third imaginary concentric ring of the plurality of imaginary concentric rings around the ultrasound probe.

EE 3: The skincare device of EE 2, wherein each of the two or more first electrical stimulation electrodes spans less than half of the first imaginary concentric ring but more than quarter of the first imaginary concentric ring.

EE 4: The skincare device of EE 2, wherein each of the plurality of radio frequency electrodes spans less than half of the second imaginary concentric ring but more than quarter of the second imaginary concentric ring.

EE 5: The skincare device of EE 2, wherein each of the two or more second electrical stimulation electrodes spans less than half of the third imaginary concentric ring but more than quarter of the third imaginary concentric ring.

EE 6: The skincare device of EE 2, wherein a shortest distance between the first imaginary concentric ring and the second imaginary concentric ring is equal to a shortest distance between the second imaginary concentric ring and the third imaginary concentric ring.

EE 7: The skincare device of EE 1, wherein the two or more second electrical stimulation electrodes are separated from each other by two or more third gaps that are not aligned with any of the two or more second gaps along a radial direction from the ultrasound probe.

EE 8: The skincare device of EE 7, wherein each of the two or more third gaps is aligned with one of the two or more first gaps along a radial direction from the ultrasound probe.

EE 9: The skincare device of EE 1, wherein each of the plurality of radio frequency electrodes is longer than any of the two or more first electrical stimulation electrodes.

EE 10: The skincare device of EE 1, wherein each of the two or more second electrical stimulation electrodes is longer than any of the plurality of radio frequency electrodes.

EE 11: A method of using the skincare device of EE 1, the method comprising activating the first treatment mode by pressing a button.

EE 12: The method of EE 11, further comprising moving the skincare device across an area on an operator's skin while the skin-contacting surface of the skincare device is touching the operator's skin and while the skincare device is in the first treatment mode.

EE 13: The method of EE 11, further comprising causing the skincare device to transition from the first treatment mode to the second treatment mode by pressing the button.

EE 14: The method of EE 13, further comprising moving the skincare device across an area on an operator's skin while the skin-contacting surface of the skincare device is touching the operator's skin and while the skincare device is in the second treatment mode.

EE 15: The method of EE 13, further comprising causing the skincare device to transition from the second treatment mode to the third treatment mode by pressing the button.

EE 16: The method of EE 15, further comprising moving the skincare device across the area on the operator's skin while the skin-contacting surface of the skincare device is touching the operator's skin and while the skincare device is in the third treatment mode.

EE 17: The method of EE 15, further comprising causing the skincare device to transition from the third treatment mode to the fourth treatment mode by pressing the button.

EE 18: The method of EE 17, further comprising moving the skincare device across the area on the operator's skin while the skin-contacting surface of the skincare device is touching the operator's skin and while the skincare device is in the fourth treatment mode.

EE 19: The method of EE 17, further comprising causing the skincare device to transition from the fourth treatment mode to the first treatment mode by pressing the button.

EE 20: The method of EE 17, further comprising turning off the skincare device by pressing the button without causing the skincare device to transition to the first treatment mode.

Other Considerations

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, and that various changes in form and details may be made without departing from the spirit and scope of the present disclosure as set forth in the following claims.

What is claimed is:
1. A skincare device, comprising:
a body having a skin-contacting surface configured to contact a user's skin;
an ultrasound probe configured to generate ultrasound waves;
a plurality of radio frequency electrodes configured to generate radio frequency waves;
a plurality of electrical stimulation electrodes configured to generate electrical impulses and negative ions, the plurality of electrical stimulation electrodes comprising two or more first electrical stimulation electrodes and two or more second electrical stimulation electrodes;

a plurality of light emitting diodes configured to emit light;

circuitry housed in the body and comprising at least one processor and at least one memory;

wherein the ultrasound probe, the plurality of radio frequency electrodes, and the plurality of electrical stimulation electrodes are collectively referred to as skincare electrodes, wherein the skincare electrodes and the plurality of light emitting diodes are arranged to provide the skin-contacting surface in which (1) the ultrasound probe is positioned in a central portion of the skin-contacting surface, (2) each of the two or more first electrical stimulation electrodes is elongated and curved around the ultrasound probe, (3) the two or more first electrical stimulation electrodes are separated from each other by two or more first gaps and further separated from the ultrasound probe by an electrically insulating material, (4) each of the plurality of radio frequency electrodes is elongated and curved around the ultrasound probe and the two or more first electrical stimulation electrodes, (5) the plurality of radio frequency electrodes are (i) separated from each other by two or more second gaps that are not aligned with any of the two or more first gaps along a radial direction from the ultrasound probe and (ii) further separated from the two or more first electrical stimulation electrodes by the electrically insulating material, (6) each of the two or more second electrical stimulation electrodes is elongated and curved around the ultrasound probe, the two or more first electrical stimulation electrodes, and the plurality of radio frequency electrodes, (7) the two or more second electrical stimulation electrodes are separated from each other and further separated from the plurality of radio frequency electrodes by the electrically insulating material, and (8) the plurality of light emitting diodes are located between two adjacent ones of the skincare electrodes and underneath the electrically insulating material separating the skincare electrodes, such that all of the skincare electrodes are configured to simultaneously contact the user's skin and the plurality of light emitting diodes are configured to deliver light to the user's skin through the electrically insulating material to apply a plurality of skincare treatments to the user's skin using the plurality of light emitting diodes and at least part of the skincare electrodes, wherein the at least one processor is programmed to activate a plurality of skincare treatment modes corresponding to the plurality of skincare treatments, the plurality of skincare treatment modes comprising a first treatment mode, a second treatment mode, a third treatment mode, and a fourth treatment mode, wherein (i) in the first treatment mode, the at least one processor causes the skincare device to simultaneously deliver light of a first color and ultrasound waves without delivering electrical impulses, radio frequency waves, and negative ions, (ii) in the second treatment mode, the at least one processor causes the skincare device to simultaneously deliver light of the first color, ultrasound waves, and electrical impulses, without delivering radio frequency waves and negative ions, (iii) in the third treatment mode, the at least one processor causes the skincare device to simultaneously deliver light of a second color different from the first color, electrical impulses, and radio frequency waves without delivering ultrasound waves and negative ions, and (iv) in the fourth treatment mode, the at least one processor causes the skincare device to simultaneously deliver light of a third color different from the first color and the second color, ultrasound waves, and negative ions without delivering electrical impulses and radio frequency waves.

2. The skincare device of claim 1, wherein the two or more first electrical stimulation electrodes form portions of a first imaginary concentric ring of a plurality of imaginary concentric rings around the ultrasound probe, the plurality of radio frequency electrodes form portions of a second imaginary concentric ring of the plurality of imaginary concentric rings around the ultrasound probe, and the two or more second electrical stimulation electrodes form portions of a third imaginary concentric ring of the plurality of imaginary concentric rings around the ultrasound probe.

3. The skincare device of claim 2, wherein each of the two or more first electrical stimulation electrodes spans less than half of the first imaginary concentric ring but more than quarter of the first imaginary concentric ring.

4. The skincare device of claim 2, wherein each of the plurality of radio frequency electrodes spans less than half of the second imaginary concentric ring but more than quarter of the second imaginary concentric ring.

5. The skincare device of claim 2, wherein each of the two or more second electrical stimulation electrodes spans less than half of the third imaginary concentric ring but more than quarter of the third imaginary concentric ring.

6. The skincare device of claim 2, wherein a shortest distance between the first imaginary concentric ring and the second imaginary concentric ring is equal to a shortest distance between the second imaginary concentric ring and the third imaginary concentric ring.

7. The skincare device of claim 1, wherein the two or more second electrical stimulation electrodes are separated from each other by two or more third gaps that are not aligned with any of the two or more second gaps along a radial direction from the ultrasound probe.

8. The skincare device of claim 7, wherein each of the two or more third gaps is aligned with one of the two or more first gaps along a radial direction from the ultrasound probe.

9. The skincare device of claim 1, wherein each of the plurality of radio frequency electrodes is longer than any of the two or more first electrical stimulation electrodes.

10. The skincare device of claim 1, wherein each of the two or more second electrical stimulation electrodes is longer than any of the plurality of radio frequency electrodes.

11. A method of using the skincare device of claim 1, the method comprising activating the first treatment mode by pressing a button.

12. The method of claim 11, further comprising moving the skincare device across an area on an operator's skin while the skin-contacting surface of the skincare device is touching the operator's skin and while the skincare device is in the first treatment mode.

13. The method of claim 11, further comprising causing the skincare device to transition from the first treatment mode to the second treatment mode by pressing the button.

14. The method of claim 13, further comprising moving the skincare device across an area on an operator's skin while the skin-contacting surface of the skincare device is touching the operator's skin and while the skincare device is in the second treatment mode.

15. The method of claim 13, further comprising causing the skincare device to transition from the second treatment mode to the third treatment mode by pressing the button.

16. The method of claim 15, further comprising moving the skincare device across the area on the operator's skin while the skin-contacting surface of the skincare device is touching the operator's skin and while the skincare device is in the third treatment mode.

17. The method of claim 15, further comprising causing the skincare device to transition from the third treatment mode to the fourth treatment mode by pressing the button.

18. The method of claim 17, further comprising moving the skincare device across the area on the operator's skin while the skin-contacting surface of the skincare device is touching the operator's skin and while the skincare device is in the fourth treatment mode.

19. The method of claim 17, further comprising causing the skincare device to transition from the fourth treatment mode to the first treatment mode by pressing the button.

20. The method of claim 17, further comprising turning off the skincare device by pressing the button without causing the skincare device to transition to the first treatment mode.

\* \* \* \* \*